US006410522B1

(12) United States Patent
Ruenberg

(10) Patent No.: US 6,410,522 B1
(45) Date of Patent: Jun. 25, 2002

(54) ANTI-DEPRESSANT, STRESS SUPPRESSOR AND MOOD IMPROVER

(75) Inventor: David Ruenberg, Haifa (IL)

(73) Assignee: Lipogen Ltd., Haifa (IL)

( * ) Notice: Subject to any disclaimer, the term of this patent is extended or adjusted under 35 U.S.C. 154(b) by 0 days.

(21) Appl. No.: 09/897,034

(22) Filed: Jul. 3, 2001

(30) Foreign Application Priority Data

Oct. 23, 2000 (IL) .................................................. 139224

(51) Int. Cl.$^7$ ............................................... A61K 31/66
(52) U.S. Cl. ....................................... 514/114; 514/143
(58) Field of Search ................................ 514/143, 114

(56) References Cited

FOREIGN PATENT DOCUMENTS

WO          WO 97/41874          11/1997

OTHER PUBLICATIONS

"Chronic phosphatidylserine treatment improves spatial memory and passive avoidance in aged rats" Zanotti et al, Psychopharmacology (1989) 299: pp. 316–321.

"Blunting by chronic phosphatidylserine administration of the stress–induced activation of the hypothalamo–pituitary–adrenal axis in healthy men" Monteleone et al, EurJ Clin Pharmacol (1992) 41 pp. 385–388.

"Effects of phosphatidylserine on the Neuroendocrine Response to Physical Stress in Humans" Monteleone et al, Neuroendocinology, 52, pp. 243–248 1990.

"Preperation of phospholipase analogs by phospholipase D" (Methods in Enzymology vol. 72, pp. 632–639, 1981).

"Expression of a high–affinity serotonin transporter in human lymphocytes" Int J. Immunopharm V.16, No. 7, pp. 561–567, 1994.

"Binding of [3H]–dopamine to human lymphocytes: Possible relationship to Neurotransmitter Uptake Sites" Faraj et al, Pharmacology v. 42, pp. 135–141, (1991).

"Role of serotonin in the pathophysiology of depression: Focus on the serotonin transporter" Clin.Chem v.40, pp. 288–295, (1994).

*Primary Examiner*—William R. A. Jarvis
(74) *Attorney, Agent, or Firm*—Mark M. Friedman

(57) ABSTRACT

An anti-depressant, mental & emotional stress suppressor and mood improver having a prominent action for decreasing blood cortisol level and serotonin reuptake and has an effect of alleviating symptoms associated with depression and mental & emotional stress of a subject administered with the improver. The improver contains as the effective ingredient a combination of phosphatidy-L-serine and phosphadtidic acid, or the salts thereof, comprising at least 20% (w/w) phosphatidy-L-serine and typically within the range of about 20%–40% of phosphatidy-L-serine, out of the total phospholipid content of the composition and at least 3% (w/w) of phosphatidic acid, preferably above about 10% and typically within the range of about 20%–40% of phosphatidic acid, out of the total phospholipid content of the composition. The phosphatidyl-L-serine and phosphatidic acid has a structural fatty acid chain derived from at least one raw material lecithin selected from the group consisting of soy bean lecithin, rapeseed lecithin or egg yolk lecithin. Using the raw material lecithin as the substrate, phosphatidyl-L-serine and phosphatidic acid can be produced by enzymatic conversion utilizing phospholipase-D.

8 Claims, No Drawings

ANTI-DEPRESSANT, STRESS SUPPRESSOR AND MOOD IMPROVER

FIELD AND BACKGROUND OF THE INVENTION

The present invention relates to a composition having an effect of alleviating symptoms associated with depression and mental and emotional stress.

A. Zanotti et al. report that the oral administration of phosphatidylserine extracted from bovine brain to aged rats with memory deficits for 12 weeks improved the performance of the aged rats (A. Zanotti et al., *Psychopharmacology Berl.*, Vol. 99, P. 316, 1989).

Monteleoni et al., (*Eur. J. Clin. Pharmacology*, 385–388, 1992) investigated the chronic administration of brain cortex phosphatidylserine on the neuroendocrine responses to physical stress. The study showed that oral administration of phosphatidylserine at 800 mg per day for 10 days prior to exercise, reduced the ACTH and cortisol responses to physical exercise. A 400 mg per day dose was shown to produce no effect on the cortisol response.

Monteleoni et al. further reported (*Neuroendocrinology*, 52, 243–248, 1990) on the influence of brain cortex phosphatidylserine on the neuroendocrine and neurovegetative responses to physical stress. In a double blind study, every participant received intravenously brain cortex phosphatidylserine or a placebo before starting a physical exercise. Blood samples were collected before and after the exercise for plasma ACTH, cortisol and growth hormone readings. It outcome showed that in the placebo group the physical stress induced an increase in ACTH, cortisol and growth hormone while the phosphatidylserine group showed a reduction in production of ACTH and cortisol.

In a series of patents (PCT No. PCT/IL97/00147 Sec. 371 Date Feb. 24, 1999 Sec. 102(e) Date Feb. 24, 1999 PCT Filed May 6, 1997 PCT Pub. No. WO97/41874 PCT Pub. Date Nov. 13, 1997, Priority Number(s): IL19960118180 19960508; WO1997IL00147 19970506) phosphatidic acid has been shown to alleviate withdrawal symptoms associated with addiction (cigarettes, alcohol, narcotics).

REFERENCES

A. Zanotti et al, "Chronic phosphatidylserine treatment improves spatial memory and passive avoidance in aged rats", *Psychopharmacology*, 99, 316–321, 1989.

Monteleone, et al., "Blunting by chronic phosphatidylserine administration of the stress-induced activation of the bypothalamo-pituitary-adrenal axis in healthy men", *Eur. J. Clin. Pharmacology*, 385–388, 1992.

Monteleone, et al., "Effects of Phosphatidylserine on the Neuroendocrine Response to Physical Stress in Humans", *Neuroendocrinology*, 52, 243–284, 1990.

Eibl A. and Kovatchev S. "Preparation of phospholipids analogs by phospholipase D." (*"Methods in Enzymology"* Vol. 72, pages: 632–639, 1981).

Faraj, B. A., Olkowski, Z. L., Jackson, R. T. Expression of a high-affinity serotonin transporter in human lymphocytes. *Int. J. Immunopharm.* 16, 561–567, 1994.

Faraj, B. A., Olkowski, Z. L., Jackson, R. T. Binding of [3H]-dopamine to human lymphocytes: possible relationship to neurotransmitter uptake sites. *Pharmacology*, 42, 134–141, 1991.

Owens, M. J., Nemeroff, C. B., "Role of serotonin in the pathophysiology of depression: focus on the serotonin transporter". *Clin. Chem.* 40, 288–295, 1994.

PCT No. PCT/IL97/00147 Sec. 371 Date Feb. 24, 1999 Sec. 102(e) Date Feb. 24, 1999 PCT Filed May 6, 1997 PCT Pub. No. WO97/41874 PCT Pub. Date Nov. 13, 1997, Priority Number(s): IL19960118180 19960508; WO1997IL00147 19970506

SUMMARY OF THE INVENTION

It is an object of the present invention to provide an improver having an effect of alleviating symptoms associated with depression and mental and emotional stress.

According to the research work of the present inventors, it is confirmed that a complex of phosphatidyl-L-serine and phosphatidic acid produced by an enzymatic conversion utilizing phospholipase-D of at least one raw material lecithin selected from the group consisting of soybean lecithin, rapeseed lecithin, and egg yolk lecithin, has in mental and emotional stress and depression a prominent effects of decreasing cortisol blood level and serotonin uptake to normal level.

An improver of the present invention contains phosphatidyl-L-serine and phosphatidic acid or the salt thereof as the effective ingredient, wherein the phosphatidyl-L-serine and phosphatidic acid have a structural fatty acid chain derived from at least one raw material lecithin selected from the group consisting of soy bean lecithin, rapeseed lecithin, and egg yolk lecithin.

The improver of the present invention may be administered effectively via intravenous administration and oral administration. The improver may be mixed with other excipients such as additional phospholipids and lysophospholoipids, sugar and protein to prepare capsules and granules with improved handling and shelf life. Because of the absence of any safety problem, the improver may be blended into daily foods and beverages, either in powder or liquid form or as hydrogenated substance for use in improving and preventing mental and emotional stress and depression symptoms.

The aforementioned phosphatidyl-L-serine and phosphatidic acid as the effective ingredients in accordance with the present invention are both produced by the enzymatic reaction with phospholipase-D using as the substrate soy bean lecithin, rapeseed lecithin or egg yolk lecithin.

The process will now be illustrated. A raw material lecithin (namely, phosphatidylcholine) selected from soy bean lecithin, rapeseed lecithin and egg yolk lecithin is subjected to the process of transphosphatidylation and hydrolysis with phospholipase-D in the presence of L-serine and water, thereby substituting the choline group with the serine group or the hydroxyl group, to produce the rearranged phosphatidyl-L-serine and phosphatidic acid.

Any commercially available soy bean lecithin, rapeseed lecithin or egg yolk lecithin may be used, with no limitation, as the raw material. As phospholipase-D for use in the process of enzymatic conversion, use may be made of for example those from cabbage and actinomyces, if they have an activity on lecithin or hydrogenated lecithin or lysolecithin in the presence of L-serine and water to produce phosphatidyl-L-serine and phosphatidic acid.

A specific process of enzymatic conversion is known and described in for example the article by Eibl A. and Kovatchev S. "Preparation of phospholipids analogs by phospholipase-D." (*"Methods in Enzymology"* Vo. 72, pages: 632–639, 1981), so no detailed explanation is described herein.

DESCRIPTION OF THE PREFERRED EMBODIMENTS

EXAMPLE 1—1

Using soybean lecithin as the raw material, phosphatidyl-L-serine and phosphatidic acid were produced by the following process.

Soybean lecithin (50 g; Epikuron 135 as the product name; Lucas Meyer GmbH, Germany) and soybean oil (10 g) were placed in a 300-ml vial, followed by addition of ethyl acetate (50 ml) for solubilization. Adding a solution (20 ml) of 0.30 g/ml L-serine dissolved in 0.1 M sodium phosphate buffer, pH 7.0 to the resulting solution for thorough blending, a solution of 500 U/ml phospholipase-D from cabbage was added to the mixture solution for reaction at 25 degrees C. for 5 hours under stirring with a stirrer.

So as to inactive the enzyme in the reaction solution, the vial containing the reaction solution was immersed in hot water. Subsequently, the reaction solution was cooled in ice to separate the solution into two layers, which were then left to stand for 30 minutes. Subsequently, the upper layer was discarded. The remaining lower layer was extracted in chloroform, which was then dried under reduced pressure.

EXAMPLE 1-2

Using egg yolk lecithin (DS-PL95E as the product name; manufactured by Doosan Corp. Venture BG Biotech BU. Korea) as the substrate, rearranged phosphatidyl-L-serine and phosphatidic acid were produced by the same method as in Example 1—1.

EXAMPLE 2-1

Soybean lecithin (Epikuron 135 as the product name; Lucas Meyer GmbH, Germany) was processed for hydrogenation. Using the hydrogenated soy bean lecithin as the substrate, phosphatidyl-L-serine and phosphatidic acid were produced by the same method as in Example 1—1.

EXAMPLE 2—2

The soybean lecithin-derived phosphatidyl-L-serine and phosphatidic acid were (1 g) produced in Example 1—1, was solubilized in a mixture solution of n-hexane (15 g) and ethanol (3 g). Adding 10% palladium carbon (0.15 g) to the solution, the resulting solution was processed for hydrogenation for about 5 hours under stirring under the conditions of room temperature and ambient pressure.

EXAMPLE 3

As will be described below, the effect of improving mood and depression level via oral administration was confirmed at a test. phosphatidyl-L-serine and phosphatidic acid complex at a ratio of 1:1 (M/M) was prepared by Lipogen Products (9000) Ltd. via the process of enzymatic reaction from a substrate soy bean lecithin according to Example 1—1. Five volunteers with depression symptoms received 200 mg. three times per day for a period of four weeks. The results are presented in the following table 1.

TABLE 1

| Subject | Age | Depression symptoms before* | Depression symptoms after* |
|---|---|---|---|
| Male | 50 | ++ | + |
| Male | 61 | ++ | 0 |
| Female | 53 | + | 0 |
| Female | 35 | ++ | + |
| Female | 42 | ++ | + |

*0 - Normal
+ Slightly depressed.
++ Highly depressed.
The depression scale was assessed by the subject.

As indicated in Table 1, a significant improvement was observed in all five participants irrespective of age or gender.

EXAMPLE 4

As will be described below, the effect of reduction of blood cortisol level under mental and emotional stress via oral administration was confirmed at a test. phosphatidyl-L-serine and phosphatidic acid complex at a ratio of 1:1 (M/M) was prepared by Lipogen Products (9000) Ltd. via the process of enzymatic reaction from a substrate soy bean lecithin according to Example 1—1. Four student volunteers in a period of critical examination with stress symptoms received 200 mg. three times per day for a period of one week. The results are presented in the following table 2.

TABLE 2

| Subject | Age | Blood cortisol level before (nM). | Blood cortisol level after (nM). |
|---|---|---|---|
| Male | 24 | 10 | 2 |
| Male | 26 | 22 | 8 |
| Female | 23 | 18 | 4 |
| Female | 35 | 12 | 8 |

Remark:
The cortisol level was measured by conventional enzyme immunoassay.

As indicated in Table 2, the cortisol level was significant reduced and approached normal level improvement was observed in all four participants irrespective of age or gender.

EXAMPLE 5

As will be described below, the effect of phosphatidyl-L-serine and phosphatidic acid complex at a ratio of 1:1 (M/M) on serotonin uptake after oral administration was confirmed at a test. phosphatidyl-L-serine and phosphatidic acid complex at a ratio of 1:1 (M/M) was prepared by Lipogen Products (9000) Lit. via the process of enzymatic reaction from a substrate soy bean lecithin according to Example 1—1. Five volunteers with depression symptoms received 200 mg. three times per day for a period of four weeks. Peripheral blood samples obtained from the subjects presented in Example 3, were separated to leucocytes, and serotonin uptake was measured with tritiated serotonin as described by Faraj et al. (*Int. J. Immunopharm.* 16, 561–567, 1994). The results are presented in the following table 3.

TABLE 3

| Subject | Age | Change in sertonin uptake level |
|---|---|---|
| Male | 50 | −40% |
| Male | 61 | −20% |
| Female | 53 | −15% |
| Female | 35 | −55% |
| Female | 42 | −58% |

As indicated in Table 3, the sertonin uptake level was significant reduced due to the treatment with the improver in all five participants irrespective of age or gender. The results with the leucocytes represents the expected changes in the brain (*Faraj et al. Pharmacology.* 42, 135–141, 1991). Such a reduction in serotonin uptake can be implicated in various positive aspects of mood improvement (Owens & Nemeroff, *Clin. Chem.* 40, 288–295, 1994).

As has been described above, the anti-depressant, mental & emotional stress suppressor and mood improver containing phosphatidyl-L-serine and phosphatidic acid from soy bean, rapeseed or egg yolk as the effective ingredient in accordance with the present invention can be continuously administered readily with no pain because phosphatidyl-L-serine and phosphatidic acid effective for improving and alleviating symptoms associated with depression and mental & emotional stress can be orally ingested from the improver. Furthermore, the phosphatidyl-L-serine and phosphatidic acid effective for improving and alleviating symptoms associated with depression and mental & emotional stress can be produced at less cost and additionally at a large scale, by utilizing enzymatic conversion via a phospholipid degradation enzyme (phospholipase-D).

What is claimed is:

1. A pharmaceutical or nutritional composition for treating depression, for suppressing mental & emotional stress and for improving mood comprising Phosphatidyl-L-serine and Phosphatidic acid or salts thereof as the effective ingredients, comprising at least 20% (w/w) Phosphatidyl-L-serine out of the total phospholipid content of the composition and at least 3% (w/w) of Phosphatidic acid out of the total phospholipid content of the composition, wherein the Phosphatidyl-L-serine and Phosphatidic acid have a structural fatty acid chain derived from at least one raw material lecithin selected from the group consisting of soy bean lecithin, rapeseed lecithin, and egg yolk lecithin, and which is produced by reaction with Phospholipase-D.

2. The composition of claim 1 which also contains a pharmaceutical or food excipient.

3. A method for improving symptoms of depression, mental & emotional stress and mood in a subject in need thereof comprising administering to said subject an effective amount of the composition of claim 1.

4. A method for improving symptoms of depression, mental & emotional stress and mood in a subject in need thereof by reducing the blood cortisol level and serotonin reuptake in the brain of said subject, comprising administering an effective amount of the composition of claim 1 to said subject.

5. A pharmaceutical or nutritional composition for treating depression, for suppressing mental & emotional stress and for improving mood comprising Phosphatidyl-L-serine and Phosphatidic acid or salts thereof as the effective ingredients, comprising at least 20% (w/w) Phosphatidyl-L-serine out of the total phospholipid content of the composition and at least 3% (w/w) of Phosphatidic acid out of the total phospholipid content of the composition, wherein the Phosphatidyl-L-serine and the Phosphatidic acid have a structural fatty acid chain derived from at least one raw material lecithin selected from the group consisting of soy bean lecithin, rapeseed lecithin, and egg yolk lecithin and which is produced by reaction with Phospholipase-D and wherein the structural fatty acid chain is a hydrogenated saturated fatty acid chain.

6. The composition of claim 5 which also contains a pharmaceutical or food excipient.

7. A method for improving symptoms of depression, mental & emotional stress and mood in a subject in need thereof comprising administering to said subject an effective amount of the composition of claim 5.

8. A method for improving symptoms of depression, mental & emotional stress and mood in a subject in need thereof by reducing the blood cortisol level and serotonin reuptake in the brain of said subject, comprising administering an effective amount of the composition of claim 5 to said subject.

* * * * *

UNITED STATES PATENT AND TRADEMARK OFFICE
CERTIFICATE OF CORRECTION

PATENT NO. : 6,410,522 B1
DATED : June 25, 2002
INVENTOR(S) : Rutenberg

It is certified that error appears in the above-identified patent and that said Letters Patent is hereby corrected as shown below:

<u>Title page,</u>
Please correct the typographical error in Item [12] and [75]. Inventor should be shown as: -- Rutenberg -- and not as appears "Ruenberg"

Signed and Sealed this

Twenty-ninth Day of October, 2002

Attest:

Attesting Officer

JAMES E. ROGAN
*Director of the United States Patent and Trademark Office*